US010781470B2

(12) United States Patent
Malo

(10) Patent No.: US 10,781,470 B2
(45) Date of Patent: Sep. 22, 2020

(54) DIAGNOSIS AND TREATMENT OF INCIPIENT DIABETES

(71) Applicant: Madhu S. Malo, Burlington, MA (US)

(72) Inventor: Madhu S. Malo, Burlington, MA (US)

(*) Notice: Subject to any disclaimer, the term of this patent is extended or adjusted under 35 U.S.C. 154(b) by 413 days.

(21) Appl. No.: 14/943,155

(22) Filed: Nov. 17, 2015

(65) Prior Publication Data
US 2016/0201110 A1 Jul. 14, 2016

Related U.S. Application Data

(60) Provisional application No. 62/101,751, filed on Jan. 9, 2015.

(51) Int. Cl.
C12Q 1/42 (2006.01)
A61K 35/741 (2015.01)
A23L 33/17 (2016.01)
G01N 33/68 (2006.01)
A23L 29/00 (2016.01)
A23C 9/12 (2006.01)
A61K 9/00 (2006.01)
A61K 38/46 (2006.01)
A61K 35/00 (2006.01)

(52) U.S. Cl.
CPC .............. C12Q 1/42 (2013.01); A23C 9/1216 (2013.01); A23L 29/06 (2016.08); A23L 33/17 (2016.08); A61K 9/0095 (2013.01); A61K 35/741 (2013.01); A61K 38/465 (2013.01); G01N 33/6893 (2013.01); A23V 2002/00 (2013.01); A61K 2035/115 (2013.01); C12Y 301/03001 (2013.01); G01N 2333/916 (2013.01); G01N 2800/04 (2013.01); G01N 2800/042 (2013.01); G01N 2800/32 (2013.01); Y02A 50/463 (2018.01)

(58) Field of Classification Search
CPC ....................................................... C12Q 1/42
See application file for complete search history.

(56) References Cited

U.S. PATENT DOCUMENTS 5,094,956 A * 3/1992 Grow .................... G01N 33/528
435/184
8,735,087 B2 * 5/2014 Brands .................. A23C 9/1216
435/21
2010/0093552 A1 4/2010 Panja
2011/0206654 A1 * 8/2011 Hodin .................... A61K 31/43
424/94.6
2013/0344588 A1 * 12/2013 Halushka ............. C12Q 1/6804
435/309.1

FOREIGN PATENT DOCUMENTS

EP 1487501 B1 12/2012
WO 2004046371 A2 6/2004
WO 2007079301 A2 7/2007
WO 2010025267 A2 3/2010
WO 2012054057 A1 4/2012

OTHER PUBLICATIONS

Sigma-Aldrich, "Colorimetric Alkaline Phosphatase and Peroxidase Substrate Detection Systems" (2008), BioFiles, vol. 3.4, No. 6 (Year: 2008).*
"Nitrocellulose Transfer Membranes" (2011), ThermoScientific, No. 0391.5 (Year: 2011).*
Evers, "Thyroid disorders: Metabolic diseases", (Oct. 9, 2009), Alzheimer Europe, pp. 1-4 (Year: 2009).*
Horrigan et al. "The Origins of Human Fecal Alkaline Phosphatase", (Jul. 1974), Digestive Diseases, vol. 19, No. 7: 603-608 (Year: 1974).*
International Search Report and Written Opinion for PCT/US15/61017, dated Mar. 11, 2016.
International Preliminary Report on Patentability for International Application No. PCT/US15/61017, dated Jul. 11, 2017.
K. Kaliannan et al. Intestinal alkaline phosphatase prevents metabolic syndrome in mice, Proceedings of the National Academy of Sciences, vol. 110, No. 17, Apr. 8, 2013 (Apr. 8, 2013), pp. 7003-7008.
Mehrbod Estaki, et al. Interplay between intestinal alkaline phosphatase, diet, gut microbes and immunity World Journal of Gastroenterology, vol. 20, No. 42, Jan. 1, 2014 (Jan. 1, 2014), p. 15650.
Ji Young Kim, et al. Intestinal Alkaline Phosphatase in the Colonic Mucosa of Patients with Inflammatory Bowel Disease, The Korean Society of Gastroenterology & SIDDS 2014, PS 0906, Jan. 1, 2014.
Lehmann F-G, et al. Fecal intestinal alkaline phosphatase: a parameter for toxic damage of the small intestinal mucosa. Digestion, S. Karger AG., Basel, CH, vol. 21, No. 3, Jan. 1, 1981 (Jan. 1, 1981), pp. 156-162.
Lehmann, Activity of intestinal alkaline phosphatase in feces in chronic bowel disease, Zeitschrift Fuer Gastroenterologie, Georg Thieme Verlag, DE, vol. 18, No. 4, Jan. 1, 1980 (Jan. 1, 1980), pp. 208-215.
Extended European Search Report EP Application No. 15877300.2 dated Aug. 23, 2018.
International Search Report and Written Opinion for International Application No. PCT/US2015/061017, dated Mar. 11, 2016.
Talbot et al., "Serum Phosphatase as an Aid in the Diagnosis of Cretinism and Juvenile Hypothyroidism", Am J Dis Child, 1941;62(2):273-278.

(Continued)

Primary Examiner — Teresa E Knight
(74) Attorney, Agent, or Firm — Burns & Levinson LLP; Janine M. Susan

(57) ABSTRACT

A method is described for predicting incipient diabetes, metabolic disorders or the metabolic syndrome by developing a personal temporal Phosphatase profile, which is generated by measuring phosphatase concentration in stool at a single time-point or multiple time-points. The phosphatase profile further can be used for diagnosing and determining prognosis of other incipient or overt diseases, such as the metabolic syndrome, coronary heart disease, nonalcoholic fatty liver disease, cancers, other chronic or acute diseases or infectious diseases. Also described is a specific dose of phosphatase for therapeutic use in incipient diabetes and other incipient or overt diseases.

15 Claims, 5 Drawing Sheets

(56) References Cited

OTHER PUBLICATIONS

Bozzetti et al., "Metabolic Bone Disease in preterm newborn: an update on nutritional issues", Italian Journal of Pediatrics, vol. 35, 2009, 10 pgs.
Galindo, "Alkaline Phosphatase (ALP)", Aug. 23, 2010, 4 pages.
Lan et al., "IA-2, a transmembrane protein of the protein tyrosine phosphatase family, is a major autoantigen in insulin-dependent diabetes mellitus," Proc. Natl. Acad. Sc. USA, vol. 93, pp. 6367-6370, Jun. 1996.
Appleyard et al., "Pretreatment with the probiotic VSL#3 delays transition from inflammation to dysplasia in a rat model of colitis-associated cancer," Am J Physiol Gastrointest Liver Physiol 301:G1004-G1013, 2011.

\* cited by examiner

DIAGNOSIS AND TREATMENT OF INCIPIENT DIABETES

CROSS-REFERENCE TO RELATED APPLICATIONS

This application claims priority to and benefit of U.S. Provisional Patent Application No. 62/101,751, filed Jan. 9, 2015, and entitled DIAGNOSIS AND TREATMENT OF INCIPIENT DIABETES, which is incorporated by reference herein in its entirety for all purposes.

BACKGROUND

Type 2 diabetes mellitus (T2DM) is characterized by hyperglycemia, and it is a major global health problem that affects nearly 5.3% population of the world with devastating consequences in the context of healthcare cost, morbidity and mortality (American Diabetes Association. Diagnosis and classification of diabetes mellitus. Diabetes Care. 2014 January; 37 Suppl 1:S81-90; Abdullah et al. Int J Endocrinol. 2014:593982; International Diabetes Federation, IDF Diabetes Atlas, 2012, http://(www.idf.org/diabetesatlas, http://www.idf.org/diabetesatlas/update-2014; http://www.idf.org/diabetesatlas; http://www.idf.org/diabetesatlas/update-2014; American Diabetes Association. Economic costs of diabetes in the U.S. in 2012. Diabetes Care 2013; 36:1033-1046).

T2DM is diagnosed by measuring plasma glucose levels, and a fasting plasma glucose (FPG) level>7.0 millimole/liter (126 milligram/deciliter) is considered as diagnostic for T2DM. Hyperglycemia is associated with established T2DM or with the terminal stage of development of T2DM. Therefore, measuring FPG cannot be used to predict far (years) in advance whether a person have incipient diabetes, which means that the person would develop diabetes in the nature although the current FPG value is normal. Therefore, a diagnostic protocol predicting incipient diabetes and/or other diseases is warranted. Also, therapeutic intervention of these incipient or overt diseases as well as determining the prognosis of a disease is critically important.

SUMMARY OF THE INVENTION

According to the disclosure, patients with type 2 diabetes mellitus (T2DM) have less amount of the brush-border enzyme intestinal alkaline phosphatase (IAP) in their stools compared to the control non-diabetic healthy subjects. Disclosed herein is a protocol for diagnosing the incipient diabetes and other metabolic disorders (e.g., cardiovascular diseases (coronary heart disease), cerebrovascular disease (stroke), peripheral vascular disease, nonalcoholic fatty liver disease, etc.) and the metabolic syndrome (e.g., obesity, hyperglycemia, insulin resistance, hyperinsulinemia, dyslipidemia, hypercholesterolemia, hypertriglyceridemia, low high-density lipoprotein (HDL), high low-density lipoprotein (LDL), hypertension, fatty liver, etc.) by developing a temporal profile of stool TAP levels for humans and other animals, such as cattle, pig, sheep, goats, cows, horses, dogs, cats, monkeys, rabbits, rats, mice, chickens, turkeys, etc. The temporal profile of TAP consists of IAP concentration determined at a single time-point or multiple time-points. A low IAP level or a persistent loss of IAP from a previously high level in a healthy subject is indicative of incipient diabetes, other metabolic disorders or the metabolic syndrome. Also disclosed is the use of temporal profiling of IAP for diagnosis or prognosis of the metabolic diseases, acute or chronic diseases, or infectious diseases, including but not limited to myocardial infarction, cancer, tuberculosis, salmonellosis, AIDS, hepatitis, acute or chronic kidney injury. It is also disclosed that a personal stool IAP profile of a normal healthy subject could be used as a reference IAP profile for future use.

It is also disclosed that specific doses of IAP, as an oral supplementation, can be administered to a mammal to decrease the risk of incipient diabetes, other metabolic disorders or the metabolic syndrome. The level of IAP in stool greatly varies from one individual to another individual. An individual with less than the average IAP level in control healthy humans (approx. 65 U/gm stool using the assay conditions disclosed herein) can be immediately provided with IAP supplementation, whereas an individual with a higher level of IAP can be further investigated allowing for the development of a temporal profile of IAP levels encompassing multiple time-points. It is further disclosed that TAP can be administered to a mammal for the treatment of metabolic diseases, acute or chronic diseases, or infectious diseases including but not limited to myocardial infarction, cancer, tuberculosis, salmonellosis, AIDS, hepatitis, acute or chronic kidney injury.

In an illustrative embodiment, the method for diagnosing or for determining the prognosis of incipient diabetes, an incipient metabolic disease, incipient metabolic syndrome, diabetes, metabolic disease or metabolic syndrome involves measuring the concentration of phosphatase in stool of a mammal and comparing the concentration to a normal range of concentrations.

In another illustrative embodiment, the methods further involve developing a temporal profile by measuring the concentration of phosphatase at a single time-point or multiple time-points.

In another illustrative embodiment, the phosphatase is intestinal alkaline phosphatase, placental alkaline phosphatase, tissue nonspecific alkaline phosphatase (liver/bone/kidney alkaline phosphatase), germ cell alkaline phosphatase, neutrophil alkaline phosphatase, mammalian alkaline phosphatase, a bacterial alkaline phosphatase, a fungal alkaline phosphatase, alkaline phosphatase, an acid phosphatase or a peptide with phosphatase activity.

In yet a further illustrative embodiment, in addition to measuring the concentration of phosphatase in a stool sample, a sample of saliva, urine, blood, plasma, serum, gastric fluid, intestinal fluid, ocular fluid, peritoneal fluid, vaginal fluid, or a body cavity fluid is also analyzed.

In another illustrative embodiment, the incipient diabetes or diabetes is type 2 diabetes mellitus, gestational diabetes, diabetes insipidus, or type 1 diabetes.

In another illustrative embodiment, the incipient metabolic disease or metabolic disease is a cardiovascular disease, coronary heart disease, cerebrovascular disease, stroke, peripheral vascular disease, nonalcoholic fatty liver disease, retinopathy, asthma, chronic pulmonary obstructive disease, cystic fibrosis, Alzheimer's disease, arthritis, eczema or psoriasis.

In another illustrative embodiment, the incipient metabolic syndrome or metabolic syndrome is obesity, hyperglycemia, insulin resistance, hyperinsulinemia, dyslipidemia, hypercholesterolemia, hypertriglyceridemia, low high-density lipoprotein (HDL), high low-density lipoprotein (LDL), hypertension or fatty liver.

In an illustrative embodiment, the method for decreasing the risk of or for treating incipient diabetes, incipient metabolic diseases, incipient metabolic syndrome, diabetes, metabolic diseases or metabolic syndrome involves administering an effective amount of phosphatase to a mammal in need thereof.

In another illustrative embodiment, the phosphatase is intestinal alkaline phosphatase, placental alkaline phosphatase, nonspecific tissue alkaline phosphatase (liver/bone/kidney alkaline phosphatase), germ cell alkaline phosphatase, neutrophil alkaline phosphatase, an alkaline phosphatase, a mammalian alkaline phosphatase, a bacterial alkaline phosphatase, fungal alkaline phosphatase, an alkaline phosphatase, an acid phosphatase or a peptide with phosphatase activity.

In yet another illustrative embodiment, the phosphatase is an intestinal alkaline phosphatase that is a native or recombinant isoform.

In yet another illustrative embodiment, the phosphatase is an intestinal alkaline phosphatase that is a mutant isoform.

In yet a further illustrative embodiment, the phosphatase is an intestinal alkaline phosphatase that is a native human intestinal alkaline phosphatase.

In another illustrative embodiment, the phosphatase is an intestinal alkaline phosphatase that is a recombinant human intestinal alkaline phosphatase.

In another illustrative embodiment, the phosphatase is an intestinal alkaline phosphatase that is a native calf or bovine intestinal alkaline phosphatase.

In yet another illustrative embodiment, the phosphatase is an intestinal alkaline phosphatase that is a recombinant calf or bovine intestinal alkaline phosphatase.

In yet a further illustrative embodiment, the phosphatase is administered orally, topically, subcutaneously, intradermally, intramuscularly, intravenously, vaginally or rectally.

In yet a further illustrative embodiment, the phosphatase is administered by an oral, nasal, dermal, vaginal or rectal spray.

In a still further illustrative embodiment, the phosphatase is administered before, during or after a meal.

In another illustrative embodiment, the phosphatase is administered in an amount effective to achieve a therapeutic goal of preventive (i.e. decreasing the risk of), palliative, or curative endpoint.

In a further illustrative embodiment, the phosphatase is administered in an amount effective to maintain a steady-state level of intestinal alkaline phosphatase in stool.

In yet a further illustrative embodiment, the phosphatase is administered in an amount effective to maintain a steady-state level between 1 to 650 units of intestinal alkaline phosphatase per gram stool, preferably in an amount effective to maintain a steady-state level of 65 units of intestinal alkaline phosphatase per gram stool measured using the alkaline phosphatase assay described herein.

In another illustrative embodiment, the phosphatase is in an amount of 1 to 6,500 units of phosphatase per dose.

In another illustrative embodiment, the phosphatase is dispensed in a tablet, gel, capsule, or semi-solid chewing gum.

In another illustrative embodiment, the phosphatase is dispensed in milk, food or a beverage.

In another illustrative embodiment, the phosphatase is dispensed with other medication from a group consisting of anti-diabetes, anti-hypertension, anti-cholesterol, anti-depression or antibiotics.

In another illustrative embodiment, the phosphatase is dispensed with other medication from a group consisting of up-regulators of IAP including, but not limited to, sodium butyrate, thyroid hormone, curcumin, omega-3 fatty acid or combinations thereof.

In another illustrative embodiment, the phosphatase is dispensed with other medication from a group consisting of anti-dysbiosis factors including, but not limited to, a protein or a peptide, preferably a beta-lactamase.

In another illustrative embodiment, the phosphatase is dispensed with other medication from a group consisting of probiotic bacteria.

In another illustrative embodiment, the phosphatase is an intestinal alkaline phosphatase that is highly purified, partially purified or unpurified.

In yet another illustrative embodiment, the phosphatase is administered to a subject, wherein the subject is human.

In yet a further illustrative embodiment, the phosphatase is administered to a subject, wherein the subject is a cow, pig, sheep, dog, cat, horse, monkey, cattle, chicken, turkey, rat, mouse, bird or a mammal.

In an illustrative embodiment, the method for diagnosing or for determining the prognosis of a chronic disease, an acute disease, an infectious disease, a disorder or a syndrome involves measuring the concentration of phosphatase in stool of a mammal and comparing the concentration to a normal range of concentrations.

In a further illustrative embodiment, the method for decreasing the risk of or for treating a chronic disease, an acute disease, an infectious disease, a disorder or a syndrome involves administering an effective amount of phosphatase to a mammal in need thereof.

In another illustrative embodiment, the chronic disease is Acne, Acquired Immunodeficiency Syndrome (AIDS), Ankylosing spondylitis, Asthma, Addison's disease, Allergic rhinitis, Alzheimer's Disease, Amyotrophic lateral sclerosis (ALS, Lou Gehrig's Disease), Aplastic anemia, Arthritis, Atherosclerosis, Attention Deficit Hyperactivity Disorder (ADHD, ADD), Autism Spectrum Disorder, Benign Prostatic Hypertrophy, Bipolar Mood Disorder, Bronchiectasis, Cancer, Cardiac Failure, Cardiomyopathy, Chronic Alcoholism, Chronic anemia, Chronic hepatitis, Chronic Amebiasis Chronic Obstructive pulmonary disorder, Chronic gastritis, Chronic esophagitis, Chronic oral diseases, Chronic Poisoning, Chronic renal disease, Collagen diseases, Crohn's disease, Cushing's diseases, Cystic Fibrosis, Dementia, Dermatomyositis, Depression, Dysrhythmias, Eating Disorders (Anorexia Nervosa, Bulimia Nervosa, Binge Eating), Eczema, Endometriosis, Epilepsy, Fibrosing Alveolitis, Gastro-Esophageal Reflex Disease (GERD), Glaucoma, Gout, Graves Disease, Hemophilia, Hyperlipidemia, Hyperpituitarism, Hypopituitarism, Hypophyseal Adenoma, Hypothyroidism, Idiopathic Thrombocytopenic Purpura, Menopause, Migraine, Motor Neuron Disease, Multiple Sclerosis, Muscular Dystrophy, Myasthenia Gravis, Myopathy, Neuropathy, Obesity, Obsessive Compulsive Disorder, Osteoarthritis, Osteoporosis, Paralysis (Paraplegia, Quadriplegia), Parkinson's disease, Paget's disease, Polyarteritis Nodosa, Polycystic ovarian disease, Psoriasis, Psoriatic Arthritis, Pulmonary Interstitial Fibrosis, Reflex Sympathetic Dystrophy (RSD) Syndrome, Rheumatoid Arthritis, Scleroderma, Schizophrenia, Sjögren's syndrome, Smoking and Tobacco-related Diseases, Systemic Lupus Erythematosus, Trigeminal Neuralgia, Tuberculosis, Ulcerative Colitis or Urinary incontinence.

In another illustrative embodiment, the acute disease is Acute Alcohol Poisoning, Acute Amebiasis, Acute Auditory Diseases, Acute Brain Diseases, Acute Cancers, Acute Cardiovascular Diseases, Acute Dental Diseases, Acute Dermatological Diseases, Acute Esophageal Diseases, Acute Gastrointestinal Diseases, Acute Kidney Diseases, Acute Liver Diseases, Acute Muscular Diseases, Acute Ocular Diseases, Acute Poisoning, Acute Oral Diseases, Acute Osteoarthritis, Acute Pharyngeal Diseases, Acute Prostatic Diseases, Acute Physical Injury (Trauma), Acute Peritoneal Diseases, Acute Respiratory Diseases or Acute Urogenital Diseases.

In another illustrative embodiment, the infectious disease is caused by *Bacillus anthracia, Bordetella pertussis, Borrelia burgdorferi, Brucella abortus, Brucella canis, Brucella melitensis, Brucella suis, Campylobacter jejuni, Chlamydophila pneumoniae, Chlamydia trachomatis, Chlamydophila psittaci, Clostridium botulinum, Clostridium difficile, Clostridium perfringens, Clostridium tetani, Corynebacterium diphtheriae, Entamoeba histolytica, Enterococcus faecalis, Enterococcus faecium, Escherichia coli*, Enterotoxigenic *Escherichia coli*, Enteropathogenic *E. coli*, Enterohemorrhagic *Escherichia coli* O157:H7, *Francisella tularensis*, Fungus (*Candida albicans*). *Haemophilus influenza, Helicobacter pylori, Leishmania* (Kala Azar), *Legionella pneumophila, Leptospira interrogans, Leptospira interrogans, Listeria monocytogenes, Mycobacterium leprae, Mycobacterium tuberculosis, Mycoplasma pneumoniae, Neisseria gonorrhoeae, Neisseria meningitides*, Parasites (protozoa, helminths, ectoparasites), *Plasmodium* (malaria), *Pseudomonas aeruginosa, Rickettsia rickettsia, Salmonella enterica* subsp. *Enterica, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae* or *Yersinia pestis*.

In yet another illustrative embodiment, the infectious disease is caused by Adenovinis, Coxsackievirus, Dengue virus, Ebola virus, Epstein-Barr virus, Hepatitis A virus, Hepatitis B virus, Hepatitis C virus, Herpes simplex virus, Cytomegalovinis, Human immunodeficiency virus (HIV), Influenza virus, Measles virus, Mumps virus, Human papillomavirus Human parainfluenza virus, Poliovirus, Rabies virus, Human respiratory syncytial virus, Rubella virus, Severe acute respiratory syndrome (SARS) coronavirus, Varicella zoster virus or Yellow fever virus.

In an illustrative embodiment, there is a kit for determining the concentration of phosphatase in stool, wherein the kit comprises of a tool for measuring a defined quantity of stool, a stool dilution buffer or water, a substrate for phosphatase and phosphatase assay buffer. The tool for measuring a defined quantity of stool can be, for example, a spoon or a scoop with a predetermined volume. The concentration of phosphatase is measured using a spectrophotometer, a biochemistry analyzer, a high-performance liquid chromatography (HPLC) machine, a colorimeter, a luminometer or a mechanical, biochemical, electrical or electronic device.

In an illustrative embodiment, there is a kit for determining the concentration of phosphatase in stool, wherein the kit comprises of a tool (e.g. a spoon or scoop with a predetermined volume) for measuring a defined quantity of stool, a substrate for phosphatase and phosphatase assay buffer. The stool sample is dissolved in a stool dilution buffer or water. Stool suspension, filtered or unfiltered, is then mixed with a substrate of phosphatase, waiting a specified period of time to allow a color to develop, comparing the developed color with photographs of standards and quantifying the amount of alkaline phosphatase in the biological sample. As an alternative to quantifying the amount of alkaline phosphatase by comparing the developed color to photographs of standards, the quantifying can be done by counting pixels of photographs.

In another illustrative embodiment, the phosphatase is intestinal alkaline phosphatase, placental alkaline phosphatase, tissue nonspecific alkaline phosphatase (liver/bone/kidney alkaline phosphatase), germ cell alkaline phosphatase, neutrophil alkaline phosphatase, an alkaline phosphatase, a mammalian alkaline phosphatase, a bacterial alkaline phosphatase, a fungal alkaline phosphatase, an alkaline phosphatase, an acid phosphatase or a peptide with phosphatase activity.

In another illustrative embodiment, the substrate for phosphatase is provided in liquid or solid form.

In another illustrative embodiment, the substrate for phosphatase is attached to a solid medium comprising a membrane, paper, stick, glass, plastic, a bead or a slide.

In yet a further illustrative embodiment, there is an enzyme-linked immunosorbent assay (ELISA) system for quantifying intestinal alkaline phosphatase in stool.

In yet a further illustrative embodiment, there is a CDP-star substrate (2-chloro-5-(4-methoxyspiro{1,2-dioxetane-3, 2'(5'-chloro)-tricyclo [3.3.1.13.7]decan}-4-yl)-1-phenyl phosphate disodium salt)-based luminescent phosphatase assay system for quantifying intestinal alkaline phosphatase in stool.

In yet a further illustrative embodiment, there is a malachite green-based phosphate detection system for quantifying intestinal alkaline phosphatase in stool.

In another illustrative embodiment, the method for diagnosing or for determining the prognosis of incipient diabetes, an incipient metabolic disease, incipient metabolic syndrome, diabetes, metabolic disease or metabolic syndrome involves providing a solid or liquid medium containing a substrate for phosphatase, contacting a biological sample, preferably a stool sample, with the solid or liquid medium, waiting a specified period of time to allow a color to develop, comparing the developed color with photographs of standards and quantifying the amount of alkaline phosphatase in the biological sample. As an alternative to quantifying the amount of alkaline phosphatase by comparing the developed color to photographs of standards, the quantifying can be done by counting pixels of photographs.

In another illustrative embodiment, the method for diagnosing or for determining the prognosis of incipient diabetes, an incipient metabolic disease, incipient metabolic syndrome, diabetes, metabolic disease or metabolic syndrome involves providing a solid medium for attaching a biological sample, preferably a stool sample, contacting a substrate for phosphatase with the solid medium, waiting a specified period of time to allow a color to develop, comparing the developed color with photographs of standards and quantifying the amount of alkaline phosphatase in the biological sample. As an alternative to quantifying the amount of alkaline phosphatase by comparing the developed color to photographs of standards, the quantifying can be done by counting pixels of photographs.

In yet another illustrative embodiment, the method for diagnosing or for determining the prognosis of incipient diabetes, an incipient metabolic disease, incipient metabolic syndrome, diabetes, metabolic disease or metabolic syndrome involves mixing a substrate for phosphatase with a biological sample, preferably a stool sample waiting a specified period of time to allow a color to develop, comparing the developed color with photographs of standards and quantifying the amount of alkaline phosphatase in the biological sample. As an alternative to quantifying the amount of alkaline phosphatase by comparing the developed color to photographs of standards, the quantifying can be done by counting pixels of photographs.

In another illustrative embodiment, it is anticipated that deficiency of IAP might be associated with increase in serum endotoxins (LPS, LTA, etc.), proinflammatory nucleotides (UDP, ATP, etc), cytokines (Interleukins IL-1 to IL-36; tumor necrosis factors INF-alpha, beta and gamma; interferons INF-alpha, beta and gamma; transforming growth factor TGF-beta; IFN-g inducing factor (IGIF), etc.), chemokines (CXCL-8, CCL2, CCL3, CCL4, CCL5, CCL11, CXCL10, granulocyte-macrophage colony-stimulating factor GM-CSF), granulocyte-colony stimulating factor (G-CSF), etc.), and antagonists of cytokine receptors. Further, it is anticipated that IAP deficiency might also be associated with decrease in anti-inflammatory factors such as receptors of interleukins, TNFs and INFs, and some interleukins with dual pro- and anti-inflammatory functions (IL-4, IL-6, IL-10, IL-11, IL-13, etc.).

DETAILED DESCRIPTION

Figure 1:
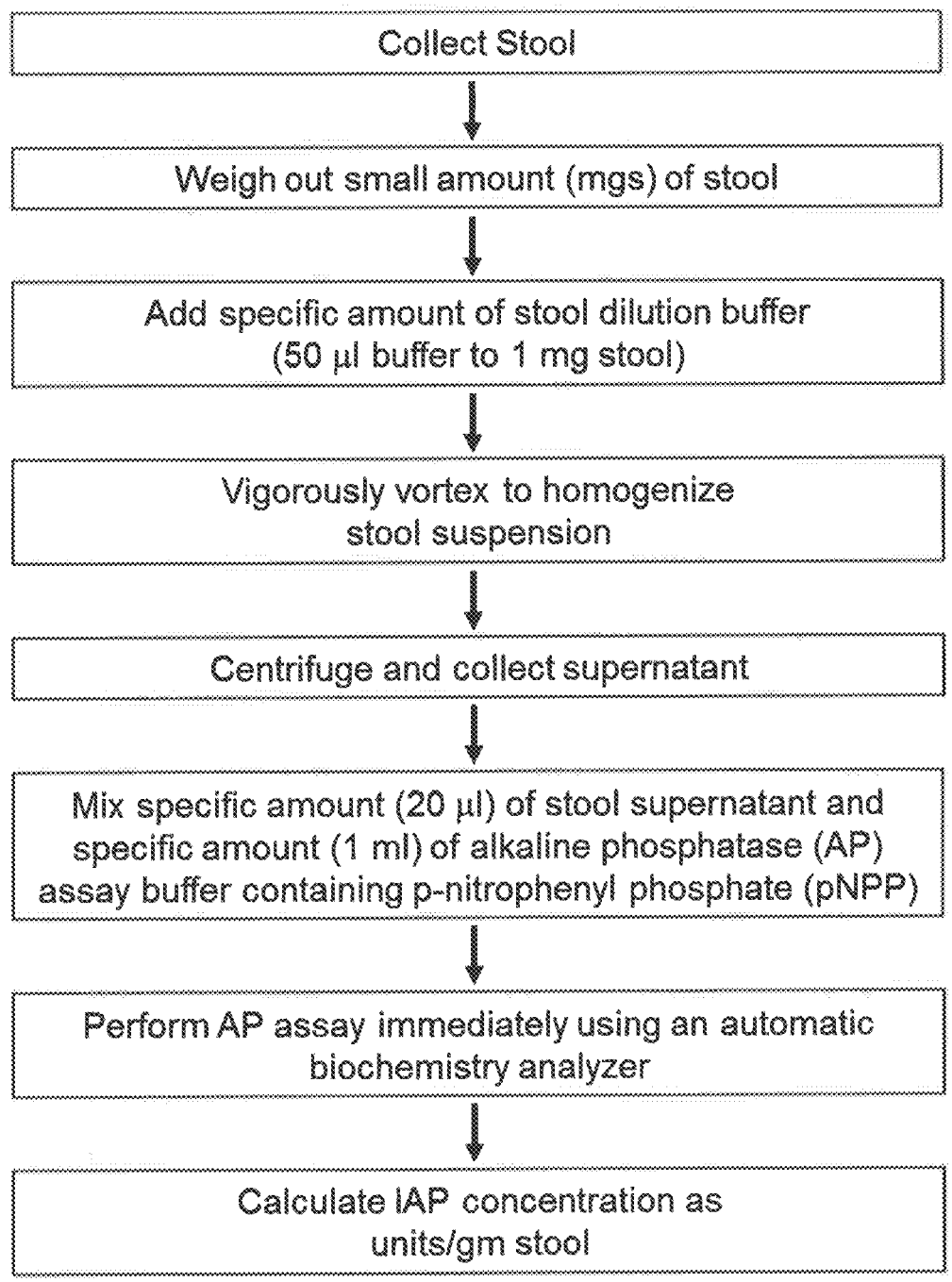
FIG. 1 is a flow chart showing the steps for determining the concentrations of intestinal alkaline phosphatase (IAP) in stool.

Type 2 diabetes mellitus: Type 2 diabetes mellitus (T2DM) is characterized by hyperglycemia resulting from defects in insulin secretion, insulin action, or both. T2DM is diagnosed as having fasting plasma glucose (FPG) level>7.0 mmol/l (126 mg/dl) or >11.1 mmol/l (200 mg/dl) of plasma glucose during oral glucose tolerance test (OGTT) performed by ingestion of 75 gm glucose and measuring plasma glucose levels at specific time intervals (min). T2DM causes long-term damage, dysfunction, and failure of different organs, especially the eyes, kidneys, nerves, heart, and blood vessels (American Diabetes Association. Diagnosis and classification of diabetes mellitus. Diabetes Care. 2014 January; 37 Suppl 1:S81-90). It is a major global health problem that affected 387 million people worldwide in 2014 and cost 612 billion US dollars (Abdullah et at Int J Endocrinol, 2014:593982; International Diabetes Federation, IDF Diabetes Atlas, 2012, http://wvw.idf.org/diabetesatlas; http://www.idf.org/diabetesatlas; update-2014). In the United States, estimated 24.4 million people (9.2% population) had diabetes in 2013, costing 306 billion dollars (http://www.idf.org/diabetesatlas; http://www.idf.org/diabetesatlas/update-2014; Abdullah et al. Int J Endocrinol. 2014: 593982). The American Diabetes Association estimated the total cost of diagnosed diabetes in 2012 as $245 billion, including $176 billion in direct medical costs and $69 billion in reduced productivity (American Diabetes Association. Economic costs of diabetes in the U.S. in 2012. Diabetes Care 2013; 36:1033-1046).

Biologically, various factors have been postulated to be involved in the development of T2DM, such as autoimmunity, the metabolic syndrome, diets, obesity, infection, ethnicity, genetic polymorphism and predisposition, drugs, stress, sedentary lifestyle, pregnancy, etc. (Kahn et al. Lancet 2014; 383(9922):1068-83; Stumvoll et al. Lancet 2005; 365(9467):1333-46; Pietropaolo et al. Diabetes 2007; 56(5); 1189-97. Bakker et al. Eur J Endocrinol 2013; 169(5):R99-R114; Lin and Sun. J Endocrinol 2009; 204(1):1-11; Leahy. Arch Med Res 2005; 36(3):197-209; DeFronzo. Med Clin North Am 2004; 88(4):787-835; Holt. Br J Psychiatry Suppl, 2004 April; 47:S55-63).

Recently, a low-grade systemic inflammation, induced by persistently increased levels of endotoxin lipopolysaccharides (LPS) in blood (metabolic endotoxemia), has been implicated as an etiological factor for the metabolic syndrome that eventually leads to T2DM (Cani et al., Diabetes 2007; 56(7):1761-72). We have shown that mice deficient in the brush-border enzyme intestinal alkaline phosphatase (IAP) develop T2DM (Kaliannan et al. Proc Natl Acad Sci USA 2013; 110(17):7003-8). We have also shown that IAP detoxifies LPS and reduces metabolic endotoxemia, and oral supplementation with IAP not only prevents but also cures high-fat diet-induced metabolic syndrome and T2DM in wild-type mice T2DM (Kaliannan et at Proc Natl Acad Sci USA 2013; 110(17);7003-8). We postulated that a low level of IAP in the intestinal lumen might be associated with T2DM in humans, and therefore, we decided to determine the levels of IAP in the stools of diabetic and healthy non-diabetic populations. In this invention, we report that, indeed, the diabetic patients have less amounts of IAP in their stools compared to the healthy non-diabetic population. Based on this observation, we propose to develop a personal temporal profile of IAP levels in stool, and if the profile of a healthy person shows that IAP levels are low and/or rapidly decreasing then we can predict that the person most probably have incipient diabetes. We anticipate that a personal temporal profile of IAP levels in stool would be highly valuable for diagnosis, treatment and assessing prognosis of any disease.

Persons having incipient diabetes currently have a FPG value in the normal range, but are at risk of developing diabetes based on a low concentration of phosphatase or a concentration of phosphatase that is persistently decreasing over time as well as other known risk factors.

The Metabolic Syndrome: The metabolic syndrome consists of a group of related disorders that includes obesity, hyperglycemia, insulin resistance, hyperinsulinemia, dyslipidemia (abnormal lipid profile), hypercholesterolemia, hypertriglyceridemia, low high-density lipoprotein (HDL), high low-density lipoprotein (LDL), hypertension and fatty liver (Kaliannan et al. Proc Natl Acad Sci USA 2013; 110(17):7003-8; Grundy et al. Circulation. 2004 Jan. 27; 109(3):433-8; Hotarnisligil. Nature 444(7120:860-867). The 'overt' metabolic syndrome has been defined as the co-existence of at least 3 out of 5 criteria encompassing obesity (body mass index (BMI)>30.0 kg/m$^2$), hyperglycemia (FPG>5.5 mmol/l), hypertension (systolic blood pressure>130 mmHg or diastolic blood pressure>85 mmHg), hypertriglyceridemia (>150 mg/dl) and low high-density lipoprotein (HDL) (<40 mg/dl for males or <50 mg/dl for females) (Huang P L. A comprehensive definition for metabolic syndrome. Dis Model Mech 2009; 2(5-6):231-7). International Diabetic Federation estimates that approximately 25% of the world population have the metabolic syndrome (Kaur. Cardiol Res Pract. 2014; 2014:943162; http://www.idf.org/metabolic-syndrome). Approximately 40% of the US population have the syndrome (Kaliannan et al. Proc Natl Acad Sci USA 2013; 110(17):7003-8; Ford. Diabetes Care. 2005 November; 28(11):2745-9). The metabolic syndrome leads to metabolic diseases such as T2DM, cardiovascular disease (coronary heart disease), cerebrovascular disease (stroke), nonalcoholic fatty liver disease, etc. The metabolic syndrome has become an epidemic in the USA with devastating consequences in terms of healthcare expenditure, morbidity and mortality (Kaliannan et al. Proc Natl Acad Sci. USA 2013; 110(17):7003-8; Malik et al. Circulation. 2004 Sep. 7; 110(10):1245-50).

Pathogenesis of the metabolic syndrome is poorly understood; however, recent work by Cani et al. (Diabetes 2007; 56:1761-1772) established that "metabolic endotoxemia" plays a critical role for the development of the metabolic syndrome. Endotoxin, also known as lipopolysaccharides (LPS), is the cell-wall component of Gram-negative bacteria. The metabolic endotoxemia is defined as a persistent increase of two- to three-fold endotoxin levels in the circulation compared to the normal levels (Cani et al. Diabetes 2007; 56:1761-1772; Kaliannan et al. Proc Natl Acad Sci USA 2013; 110(17):7003-8).

Metabolic endotoxemia causes low-grade systemic inflammation as evidenced by increased serum levels of interleukin (IL)-1, IL-6 and tumor necrosis factor-alpha (INF-$\alpha$) (Cani et al. Diabetes 2007; 56:1761-4772; Kaliannan et al. Proc Natl Acad Sci USA 2013; 110(17):7003-8). On the other hand, it is well-evidenced that chronic inflammation adversely affects the function of pancreatic beta cells (Hohmeier et. al. Int J Obes Relat Metab Disord 27(Suppl 3):S12-S16), hepatocytes (Gieling et al. Am J Physiol Gastrointest Liver Physiol 296(6):G1324-G1331), and vascular endothelial cells (Hansson. N Engl Med 352(16):1685-1695), and dysfunction of these cells is recognized to contribute to the metabolic syndrome.

Antibiotic-associated dysbiosis sometimes leads to *Clostridium difficile* infection as well as metabolic syndrome (Alam et al. Ann Surg. 2014 April; 259(4):715-22; Kaliannan et al. Proc Natl Acad Sci USA 2013; 110(17);7003-8, Parekh et al. Clin Transl Gastroenterol. 2015 Jun. 18; 6:e91). It has been shown that beta-lactamase prevents dysbiosis associated with a few specific antibiotics (Goldberg et al. Am J Health Syst Pharm. 2015 Jan. 15; 72(12):1007-12).

As described above, we have shown that IAP knockout mice develop the metabolic syndrome that ultimately leads to T2DM. We have also shown that oral IAP supplementation can prevent as well as cure the high fat diet-induced metabolic syndrome.

Persons having the incipient metabolic syndrome currently have normal or abnormal values for glucose, insulin, cholesterol, lipids, blood pressure, liver fat, BMI, etc., but are at risk of developing the metabolic syndrome based on a low concentration of phosphatase or a concentration of phosphatase that is persistently decreasing over time as well as other known risk factors.

Persons having the incipient metabolic syndrome also include persons with the pre-metabolic syndrome who have at least one criterion of the 'overt' metabolic syndrome as defined above.

Persons having incipient metabolic diseases currently have normal or abnormal metabolic function of different organs (e.g., liver, king, kidney, pancreas, brain, muscle, adrenal glands, heart, skin, etc.), but are at risk of developing metabolic diseases based on a low concentration of phosphatase or a concentration of phosphatase that is persistently decreasing over time as well as other known risk factors.

Intestinal Alkaline Phosphatase: Intestinal alkaline phosphatase (IAP) is a membrane-bound glycoprotein that is exclusively expressed in villus-associated enterocytes of proximal small intestine and hence recognized as an enterocyte differentiation marker (Hodin et al. Am J Physiol. K 1995 August; 269(2 Pt 1):C385-91; Eliakim et al. Biochim Biophys Acta. 1991 Jan. 10; 1091(19:1-8). As the name suggests, IAP optimally functions at a high pH, and it hydrolyzes monophosphate esters suggesting its important role in fat and phosphate metabolism (Malo et al. Am j Physiol Gastrointest Liver Physiol. 2006 April; 290(4): G737-46, and references therein). From the enterocytes the enzyme is bidirectionally secreted into the intestinal lumen as well as the systemic circulation (Eliakim et al. Biochim Biophys Acta. 1991 Jan. 10; 1091(1):1-8). IAP in the intestinal lumen travels downwards from the proximal small intestine to the distal large intestine and then excreted with stool (Malo et al., Gut. 2010; 59:1476-1484). IAP is strictly conserved among species (Goldstein et al. Proc Natl Mad Sci USA. 1980 May; 77(5):2857-60) indicating an essential physiological role of IAP. Various isozymes of alkaline phosphatases (APs) exist, and they include IAP, placental AP, tissue nonspecific (liver/bone/kidney/neutrophils) AP, and germ cell AP. These various AP enzymes share significant structural homology as well as functional similarities (Kaliannan et al. Proc Natl Mad Sci USA 2013; 110(17): 7003-8; Goldstein et at Proc Natl Acad Sci USA. 1980 May; 77(5);2857-60). IAP protein is a component of the surfactant-like particle (SLP), a unilamellar secreted membrane associated with the process of fat absorption and secreted from the apical surface of enterocytes (Malo et al. Am J Physiol Gastrointest Liver Physiol. 2006 April; 290(4): G737-46; Mahmood et al. Am J Physiol. Gastrointest Liver Physiol. 2003 August; 285(2):G433-41).

Physiologically, IAP exerts two very important functions with respect to its existence in the luminal bacterial environment; firstly, it maintains the normal homeostasis of intestinal microbiota, and secondly, it detoxifies bacterial toxins. We have shown that IAP knockout mice harbor fewer bacteria compared to its wild-type littermates (Malo et al., Gut. 2010; 59:1476-1484) and IAP promotes the gut bacterial growth by reducing the concentrations of intestinal luminal nucleotide triphosphates that have toxic effect on bacterial growth (Malo et al. Am J Physiol Gastrointest Liver Physiol. 2014 May 15; 306(10):G826-38). We and others have shown that IAP detoxifies various bacterial toxins, such as lipopolysaccharides (LPS), CpG DNA, flagellin and uridine diphosphate (UDP), and IAP probably destroys these targets by dephosphorylation (phosphohydrolysis) (Poelstra et at U.S. Pat. No. 6,290,952, September 2001; Bentala et al. Shock. 2002 December; 18(6):561-6; Chen et al. Am J Physiol Gastrointest Liver Physiol. 2010 August; 299(2):G467-75; Moss et al. Am J Physiol Gastrointest Liver Physiol. 2013 Mar. 15; 304(6):0597-604; Malo et al. Am J Physiol Gastrointest Liver Physiol. 2014 May 15; 306(10):G826-38). Recently, using mice deficient in IAP (IAP knockout) Narisawa et al. (Mol Cell Biol. 2003 November; 23(21):7525-30) showed that IAP limits fat absorption, and IAP knockout mice become obese when fed a high fat diet.

Pharmacologically, various therapeutical uses of IAP have been described in different animal models as well as in humans. In a mouse model, we have shown that oral supplementation of IAP prevents antibiotic-induced susceptibility to enteric pathogens such as *Salmonella Typhimurium*, and *Clostridium difficile* (Malo et al., Gut. 2010; 59:1476-1484; Alam et al. Ann Surg, 2014 April; 259(4): 715-22). We have shown that oral IAP supplementation not only prevents but also cures the high fat diet-induced metabolic syndrome in mice (Kaliannan et al. Proc Natl Acad Sci USA 2013; 110(17):7003-8). Kiss has recently claimed use of IAP to correct insulin resistance, hyperinsulinemia and dyslipidemia in a patent application with USPTO (Kiss, USPTO patent application no. US 2013/0251701 A1, Sep. 26, 2013). Kiss has also previously claimed use of IAP to treat obesity, diabetes and cancer (U.S. Pat. Nos. 7,858,085; 8,603,464 & 7,943,606).

Lukas et al. showed efficacious value of IAP in treating ulcerative colitis in humans (Lucas et al. Inflamm Bowel Dis. 2010 July; 16(7):1180-6). In mouse models we have also shown that IAP has beneficial effects to treat chronic colitis (Ramasamy et al. Inflamm Bowel Dis. 2011 February; 17(2):532-42). Whitehouse et al. reported a protective role of intestinal alkaline phosphatase in necrotizing enterocolitis (Whitehouse et al. J Surg Res. 2010 September; 163(1):79-85). Van Veen et al, showed that bovine intestinal alkaline phosphatase attenuates the inflammatory response in secondary peritonitis in mice (van Veen et al. Infect Immun. 2005 July; 73(7):4309-14). We have demonstrated that local peritoneal irrigation with IAP is protective against peritonitis in mice (Ebrahimi et al. J Gastrointest Surg. 2011 May; 15(5):860-9).

General Methodology

Participants: A case-control study was used to assess the difference in the concentrations of IAP in stools of diabetic and control non-diabetic healthy populations. Participants, aged 30-70 yr., were recruited from a suburban community of Dhaka, Bangladesh by advertisement through local dignitaries, hospitals, clinics and physicians' offices. Based on preliminary data (unpublished) the sample size of each group was calculated to achieve statistical power of 80% or more (continuous endpoint, $\alpha=0.05$). The study included 202 diabetic cases (63 males and 139 females) and 445 healthy control subjects (114 males and 331 females) of the same ethnicity. The study included more females than males just because of more accessibility to female participants. People with T2DM were diagnosed by a physician for at least 6 months prior to their recruitment, and were on oral antihyperglycemic agents and/or insulin medication. Newly diagnosed persons with hyperglycemia (FPG>7.0 mmol/l) were also included in the diabetic group (see below). All participants were on unrestricted diets. Any person suffering from an acute disease was excluded from the study. Pregnant women, patients with Type 1 diabetes and history of cancer were excluded. All participants were tested for renal, hepatic and cardiovascular diseases, and participants with clinically significant renal, hepatic and cardiovascular diseases were excluded. The participants did not have any history of chronic alcohol consumption. Underweight persons (body mass index, BMI<18.5 $kg/m^2$) were also excluded.

Study approval. An informed consent form to participate in the study was signed by each participant. The Institutional Review Board (IRB) of Harvard Biotech BD Ltd. (Dhaka, Bangladesh) reviewed and approved the study.

Laboratory tests, physical examination and socio-medical history: Laboratory tests were performed using commercially available biochemical assay kits (Linear Chemicals S. L., Barcelona, Spain) and an automatic biochemistry analyzer (Sinnowa Medical Science & Technology Co., Ltd, Nanjing, Jiangsu, China; Model: Sinnolab MT 5000, Version 5.00). The diabetic status of each participant (diabetics and controls) was confirmed by measuring fasting (at least 10 hours) plasma glucose (FPG). An FPG level>7.0 mmol/l (126 mg/dl, milligrams/deciliter), was considered diagnostic for diabetes (American Diabetes Association, 2014). Any newly diagnosed diabetic patient (FPG>7.0 mmol/l) was included in the diabetic group. All participants were also subjected to serum biochemical tests for cholesterol, low-density lipoproteins (LDL), high-density lipoprotein (HDL), triglycerides, creatinine and ALT. Height and weight of each participant were measured to calculate the body mass index (BMI) defined as weight in kg divided by the square of height in meter ($kg/m^2$). Participants were asked for the history of alcohol consumption. Medical history was used to discover participants with kidney, liver and heart diseases. The status of cardiovascular disease was also evaluated by measuring blood pressure.

Homogenization of stool: The supernatant of a homogenized stool suspension was used for IAP assay. A small amount of stool (milligrams) was measured and then the 'stool dilution buffer' (10 mM (millimolar) Tris-HCl, pH 8.0, 1 mM magnesium chloride, 10 µM (micromolar) zinc chloride) at a defined ratio was added. Usually, 50 µl (microliter) of stool dilution buffer was added to 1 mg of stool. The sample was vigorously vortexed to prepare a homogenized stool suspension, which was then centrifuged at 10,000×g for 20 min, and the supernatant containing IAP was collected and assayed for IAP concentration. Alternatively, stool can be suspended water, however, stool suspended in water shows a bit lower IAP activity as compared to stool suspended in stool dilution buffer.

Alkaline Phosphatase Assay. The stool supernatant was assayed for alkaline phosphatase (AP) following an established protocol using the automatic biochemistry analyzer mentioned above (Nanjing, Jiangsu, China). In brief, 20 of supernatant was added to 1 ml of enzyme assay buffer (1.25 M diethanolamine (DEA) buffer, pH 10.2, 0.6 mM magnesium chloride) containing 10 mM p-nitrophenyl phosphate (pNPP), and the reaction mixture was incubated for one min at 37° C. followed by measuring the AP concentration by the analyzer pre-calibrated with AP standards. To determine the major isoform among stool APs, prior to assaying for AP activity an aliquot of stool sample was treated for 10 min with L-phenylalanine (L-Phe, 10 mM final conc.), a specific inhibitor of LAP, and another aliquot with L-homoarginine (L-Arg, 10 final conc.), an inhibitor of tissue non-specific alkaline phosphatase (TNAP). Each aliquot treated with an inhibitor was then mixed with the reaction buffer containing an equal concentration (10 mM) of the respective inhibitor, and assayed for AP activity using the analyzer. Because most of the AP activity in stool was due to IAP, the stool AP values were expressed as units of IAP/g stool. All AP assays were performed by a single laboratory technologist who was blinded to the diagnoses of participants.

Statistical Analysis: The SAS System (SAS Institute, Cary, N.C.) was used for statistical analysis. Mean and standard errors were calculated for T2DM cases and non-T2DM controls stratified by sex. The correlation between IAP levels and various risk factors for T2DM was assessed via Pearson correlation coefficient stratified by sex and T2DM status (T2DM and non-T2DM controls). Mean differences in IAP levels between T2DM cases and non-T2DM controls were assessed via linear regression models controlling for the effects of age, sex, FPG and BMI on IAP levels and T2DM status. The statistical significance of the variance associated with independent variables were assessed from sum of square III using GLM procedure in SAS. Multiple logistic regression using Proc Logist procedure in SAS assessed association between T2DM cases with independent risk factors including IAP. Regression coefficients and odds ratios were used to assess the independent risk contribution of IAP to T2DM status. The statistical significance of the difference between two groups was determined using unpaired two-tailed Student's t-Test. The difference between two groups was considered significant when the p value was <0.05. Student's t-Test was performed using Microsoft Excel program. Post-hoc statistical power analysis of two independent groups was performed using an online program (http://clincalc.com/Stats/Power.aspx).

EXAMPLES

The following examples are provided to further describe the invention; however, these examples do not limit the scope of the invention defined in the claims.

Example 1

The Flow Chart Showing the Steps for Determining the Concentrations of Intestinal Alkaline Phosphatase (IAP) in Stool Mice deficient in intestinal alkaline phosphate (IAP-knockout) have been shown to develop type 2 diabetes mellitus (T2DM). Based on this observation we hypothesized that the T2DM patients might have less amount of IAP in their stools. Therefore, we planned to measure the IAP concentration in the stools of T2DM patients and control healthy participants. A schematic presentation of the protocol to determine IAP in stool is provided in FIG. 1.

Example 2

Stool Alkaline Phosphatase Activity is Mostly Due to Intestinal Alkaline Phosphatase IAP knockout ($Akp3^{-/-}$) mice develop T2DM, and based on this observation we hypothesized that humans with T2DM might have IAP deficiency. Accordingly, we decided to measure IAP concentrations in the stools of diabetic and control non-diabetic healthy people. However, taking in consideration of possible association of different isoforms of alkaline phosphatases (APs) with T2DM in humans, we first decided to determine the nature of major AP isoform in the stools of both diabetic and control healthy populations. Stool samples of non-diabetic healthy controls and T2DM patients were homogenized in a stool dilution buffer followed by centrifuging and collection of supernatant. We performed AP assays on individual aliquots of a stool sample supernatant in presence of L-phenylalanine (L-Phe, a specific inhibitor of IAP) as well as L-homoarginine (L-Arg, a specific inhibitor of TNAP).

Figure 2A:
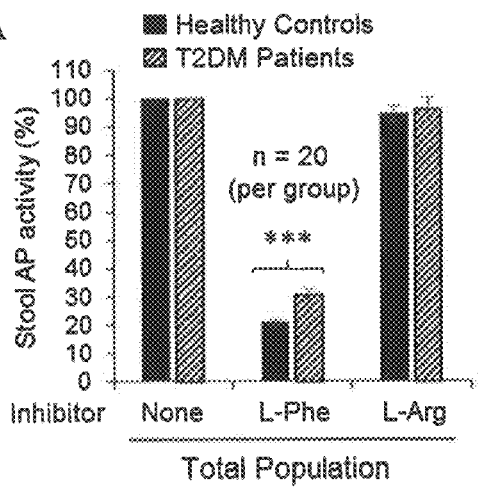
FIGS. 2A-C are graphs showing that the stool alkaline phosphatase activity is mostly due to intestinal alkaline phosphatase (IAP).
Figure 2B:
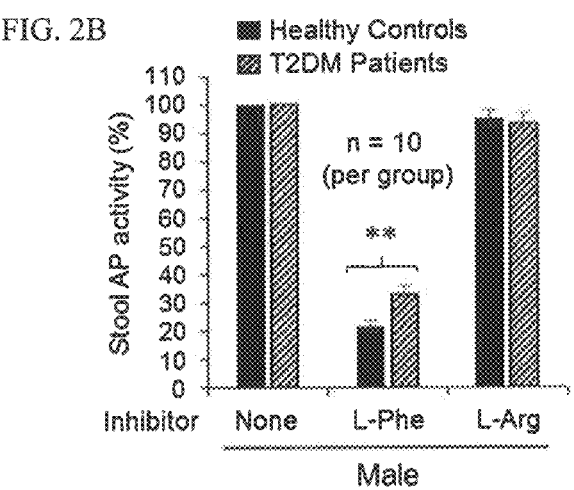
Figure 2C:
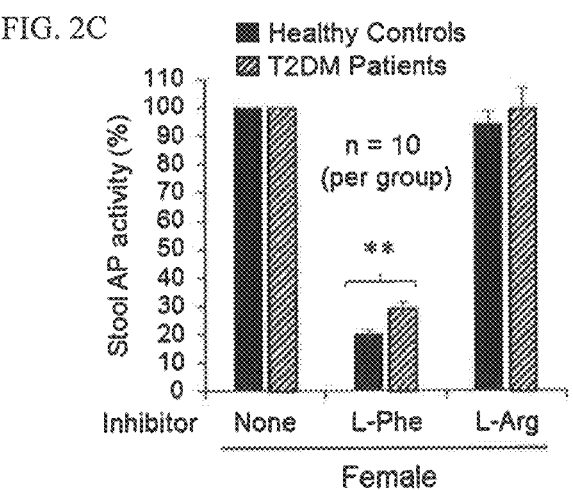

FIG. 2 is a graph showing stool alkaline phosphatase activity is mostly due to intestinal alkaline phosphatase (IAP). L-Phe inhibited approx. 80% of the AP activity in the stool of total healthy population, and the inhibition was approx. 70% in total diabetic population, however, the difference was statistically significant (p=1.4E-04) (FIG. 2A). On the other hand, L-Arg had no inhibitory effect on the stool AP activity of either group. Sex-matched distribution also showed similar AP inhibitory effect of L-Phe in males (FIG. 2B) and females (FIG. 2C) of both control and diabetic groups. This result indicates that most of the stool AP activity is due to IAP, and accordingly, we decided to refer stool AP as IAP in the following sections as it is applicable.

FIG. 2: Stool alkaline phosphatase activity is mostly due to intestinal alkaline phosphatase (IAP). Stool samples of non-diabetic healthy controls and T2DM patients were homogenized in a stool dilution buffer followed by centrifuging and collection of supernatant. The supernatant was assayed for alkaline phosphatase (AP) concentration in presence of L-phenylalanine (L-Phe), a specific inhibitor of IAP as well as in presence of L-homoarginine (L-Arg), a specific inhibitor of tissue nonspecific alkaline phosphatase (TNAP), using an automatic biochemistry analyzer. (A) Effects of AP inhibitors on the AP activity in the stools of total control and diabetic populations. (B) Effects of AP inhibitors on the AP activity in the stools of male control and diabetic populations. (C) Effects of AP inhibitors on the AP activity in the stools of female control and diabetic populations. Statistics: Values are expressed as mean+/−SEM. Statistical significance of the difference between two respective groups was tested using the unpaired two-tailed Student's t-Test. p<0.05 is considered significant. , p<0.01; *, p<0.001.

Example 3

The Levels of Intestinal Alkaline Phosphatase (IAP) is Less in the Stools of Diabetic Patients Compared to Healthy Controls Table 1 shows a few important characteristics along with the concentrations of IAP in diabetic and healthy populations. The study included 202 diabetic patients (T2DM) and 445 control healthy subjects. The diabetic group included 63 men and 139 women, whereas the control group comprised of 114 men and 331 women. The ages of the participants ranged from 30 to 70 years. A comparative analysis of IAP values of diabetic and healthy participants is provided. It is evident that compared to the total healthy population the total diabetic population has 47.6% less IAP in their stools (Mean+/−SEM: 67.4±/−3.2 vs 35.3+/−2.5 units/g stool, respectively; p=5.6E-10). Compared to healthy males, diabetic males have 51.6% less IAP (57.1+/−4.5 vs 27.7+/−3.2 units/g stool, respectively; p=1.1E-05). Similarly, in comparison to healthy females, diabetic females have 45.3% less IAP (71.0+/−4.0 vs 38.8+/−3.3 units/g stool, respectively; p 1.6E-06). It appears that healthy control males have the IAP levels 19.5% lower than the healthy females, however, the difference is not significant (p=0.061). On the other hand, the diabetic males have 28.7% lower IAP levels compared to diabetic females, and the difference is statistically significance (p=0.041). It is noteworthy that the numerical value of IAP concentration of a sample varies depending on different alkaline phosphatase assays and/or variation in assay conditions.

TABLE 1

Characteristics of healthy control participants and T2DM patients.

| Type of Participants | Total Participants | | Males | | Females | |
| --- | --- | --- | --- | --- | --- | --- |
| | Healthy | T2DM | Healthy | T2DM | Healthy | T2DM |
| No. of Participants | 445 | 202 | 114 | 63 | 331 | 139 |
| Age of Participants (yr.) | 47.1 +/− 0.4 | 47.6 +/− 0.7 | 48.7 +/− 0.8 | 50.9 +/− 1.2 | 46.7 +/− 0.5 | 46.0 +/− 0.8 |
| Weight (kg) | 59.3 +/− 0.5 | 59.6 +/− 0.7 | 65.0 +/− 0.9 | 65.7 +/− 1.3 | 57.3 +/− 0.6 | 56.9 +/− 0.8 |
| Height (m) | 1.52 +/− 0.00 | 1.52 +/− 0.01 | 1.62 +/− 0.01 | 1.61 +/− 0.01 | 1.48 +/− 0.00 | 1.48 +/− 0.01 |

TABLE 1-continued

Characteristics of healthy control participants and T2DM patients.

| Type of Participants | Total Participants | | Males | | Females | |
|---|---|---|---|---|---|---|
| | Healthy | T2DM | Healthy | T2DM | Healthy | T2DM |
| BMI (kg/m$^2$) | 25.7 +/- 0.2 | 26.0 +/- 0.3 | 24.7 +/- 0.3 | 25.5 +/- 0.5 | 26.1 +/- 0.2 | 26.2 +/- 0.4 |
| Systolic Blood Pressure (mmHg) | 134.2 +/- 1.1 | 137.3 +/- 1.5 | 134.4 +/- 1.7 | 133.3 +/- 2.5 | 134.2 +/- 1.4 | 139.0 +/- 1.8 |
| Diastolic Blood Pressure (mmHg) | 78.9 +/- 0.6 | 80.1 +/- 0.8 | 80.0 +/- 1.1 | 80.8 +/- 1.4 | 78.5 +/- 0.7 | 79.8 +/- 1.0 |
| Creatinine (mg/dl) | 0.98 +/- 0.15 | 0.91 +/- 0.02 | 0.89 +/- 0.03 | 0.95 +/- 0.03 | 1.01 +/- 0.20 | 0.89 +/- 0.03 |
| Cholesterol (mg/dl) | 162.7 +/- 1.3 | 172.5 +/- 2.2*** | 160.3 +/- 2.6 | 164.4 +/- 4.1 | 162.7 +/- 1.3 | 176.2 +/- 2.5*** |
| HDL (mg/dl) | 38.1 +/- 0.4 | 38.8 +/- 0.5 | 36.7 +/- 0.7 | 38.6 +/- 0.9 | 38.6 +/- 0.4 | 38.8 +/- 0.6 |
| LDL (mg/dl) | 94.6 +/- 1.0 | 102.2 +/- 2.0*** | 93.2 +/- 2.5 | 94.5 +/- 4.0 | 95.0 +/- 1.1 | 105.7 +/- 2.2*** |
| Triglycerides (mg/dl) | 152.2 +/- 2.3 | 159.4 +/- 3.8 | 153.5 +/- 5.9 | 162.3 +/- 7.6 | 151.7 +/- 2.4 | 158.1 +/- 4.3 |
| ALT (U/l) | 44.8 +/- 0.9 | 47.7 +/- 1.7 | 46.9 +/- 2.4 | 49.0 +/- 2.8 | 44.1 +/- 0.8 | 47.1 +/- 2.1 |
| FPG (mmol/l) | 4.4 +/- 0.0 | 8.2 +/- 0.2*** | 4.4 +/- 0.1 | 8.3 +/- 0.4*** | 4.4 +/- 0.0 | 8.2 +/- 0.3*** |
| IAP (U/g stool) | 67.4 +/- 3.2 | 35.3 +/- 2.5*** | 57.1 +/- 4.5 | 27.7 +/- 3.2*** | 71.0 +/- 4.0 | 38.8 +/- 3.3*** |

Note: The participants were recruited from a suburb of Dhaka, Bangladesh. All participants were on overnight (10 h) fasting and investigated for all the physical and biochemical tests described above. Statistics: Values are expressed as mean+/-SEM. Statistical significance of the difference between two respective groups was tested using the unpaired two-tailed Student's t-Test. $p<0.05$ is considered significant. ***, $p<0.001$. Percentage loss of IAP in T2DM patients compared to healthy controls: Total, 47.6%; Male, 51.6%; Female, 45.3%.

Table 2 shows the age group- and gender-matched distribution of stool LAP levels in the healthy control and diabetic populations. It is apparent that compared to non-diabetic group, T2DM patients have approx. 35-60% less mean stool IAP and the difference between two respective groups is statistically significant. The least reduction (36.8%) in IAP level is observed in 40-49 yr. old diabetic females, whereas the highest reduction (59.0%) is evidenced in 60-70 yr. old male diabetes patients. However, there is no statistically significant difference in IAP levels between the younger and older groups of the same population.

TABLE 2

Age group- and gender-matched distributions of IAP along with a few critical parameters of T2DM.

| Group | Type of Participants | Number of Participants | Age of Participants (years) | Body Mass Index (BMI) (kg/m$^2$) | Fasting Plasma Glucose (FPG) (mmol/l) | IAP Conc. in stool (U/gm Stool) | Loss of IAP compared to Controls (%) |
|---|---|---|---|---|---|---|---|
| 30-39 yr. old | Healthy Controls | Total: 109 | 35.7 +/- 0.1 | 27.0 +/- 0.5 | 4.5 +/- 0.1 | 78.1 +/- 7.6 | NA |
| | | Males: 22 | 36.6 +/- 0.3 | 24.8 +/- 0.6 | 4.5 +/- 0.1 | 69.9 +/- 10.2 | NA |
| | | Females: 87 | 35.5 +/- 0.1 | 27.5 +/- 0.6 | 4.4 +/- 0.1 | 80.1 +/- 9.2 | NA |
| | Diabetic Patients | Total: 43 | 35.0 +/- 0.3 | 25.8 +/- 0.7 | 7.7 +/- 0.4 | 40.6 +/- 6.1 | 48.0 |
| | | Males: 8 | 35.4 +/- 1.1 | 24.3 +/- 1.2 | 8.9 +/- 1.1 | 29.8 +/- 5.6 | 57.4 |
| | | Females: 35 | 34.9 +/- 0.3 | 26.2 +/- 0.8 | 7.5 +/- 0.4 | 43.0 +/- 7.4 | 46.3 |
| | p Value (Controls vs Diabetics) | Total | 1.2E-02 | 1.9E-01 | 5.2E-25*** | 3.6E-03** | NA |
| | | Males | 1.3E-01 | 6.6E-01 | 5.4E-07*** | 2.9E-02** | NA |
| | | Females | 4.5E-02 | 1.9E-01 | 8.2E-20*** | 1.6E-02** | NA |
| 40-49 yr. old | Healthy Controls | Total: 138 | 43.3 +/- 0.2 | 25.9 +/- 0.3 | 4.5 +/- 0.1 | 70.1 +/- 4.3 | NA |
| | | Males: 32 | 43.9 +/- 0.5 | 24.8 +/- 0.5 | 4.4 +/- 0.1 | 62.5 +/- 6.8 | NA |
| | | Females: 106 | 43.1 +/- 0.3 | 26.2 +/- 0.4 | 4.5 +/- 0.1 | 72.3 +/- 5.2 | NA |
| | Diabetic Patients | Total: 69 | 43.3 +/- 0.3 | 25.3 +/- 0.4 | 8.4 +/- 0.4 | 43.6 +/- 5.1 | 37.8 |
| | | Males: 19 | 43.9 +/- 0.6 | 25.1 +/- 0.8 | 9.0 +/- 0.8 | 38.1 +/- 7.3 | 39.1 |
| | | Females: 50 | 43.1 +/- 4.4 | 25.3 +/- 0.5 | 8.2 +/- 0.5 | 45.7 +/- 6.5 | 36.8 |
| | p Value (Controls vs Diabetics) | Total | 9.2E-01 | 2.3E-01 | 8.7E-27*** | 2.6E-04*** | NA |
| | | Males | 9.8E-01 | 7.9E-01 | 1.1E-08*** | 2.4E-02* | NA |
| | | Females | 9.9E-01 | 1.8E-01 | 3.5E-19*** | 3.1E-03** | NA |
| 50-59 yr. old | Healthy Controls | Total: 131 | 52.3 +/- 0.2 | 25.2 +/- 0.3 | 4.4 +/- 0.1 | 60.2 +/- 6.9 | NA |
| | | Males: 48 | 53.1 +/- 0.4 | 24.8 +/- 0.5 | 4.5 +/- 0.1 | 49.3 +/- 7.8 | NA |
| | | Females: 83 | 51.8 +/- 0.3 | 25.4 +/- 0.4 | 4.4 +/- 0.1 | 66.5 +/- 9.9 | NA |
| | Diabetic Patients | Total: 52 | 52.7 +/- 0.4 | 27.4 +/- 0.7 | 8.3 +/- 0.5 | 26.8 +/- 3.2 | 55.5 |
| | | Males: 21 | 54.1 +/- 0.6 | 25.8 +/- 0.6 | 8.3 +/- 0.7 | 22.5 +/- 3.9 | 54.5 |
| | | Females: 31 | 51.8 +/- 0.4 | 28.4 +/- 1.1 | 8.3 +/- 0.8 | 29.7 +/- 4.6 | 55.3 |
| | p Value (Controls vs Diabetics) | Total | 3.1E-01 | 1.2E-03** | 5.6E-22*** | 3.2E-03** | NA |
| | | Males | 1.7E-01 | 2.0E-01 | 1.4E-11*** | 3.0E-02* | NA |
| | | Females | 9.8E-01 | 1.9E-03** | 1.8E-12*** | 2.8E-02* | NA |
| 60-70 yr. old | Healthy Controls | Total: 67 | 63.0 +/- 0.4 | 24.4 +/- 0.5 | 4.4 +/- 0.1 | 58.7 +/- 6.5 | NA |
| | | Males: 12 | 63.8 +/- 0.9 | 23.3 +/- 0.9 | 4.3 +/- 0.2 | 50.3 +/- 12.3 | NA |
| | | Females: 55 | 62.9 +/- 0.5 | 24.7 +/- 0.6 | 4.4 +/- 0.1 | 60.5 +/- 7.5 | NA |

TABLE 2-continued

Age group- and gender-matched distributions of IAP along with a few critical parameters of T2DM.

| Group | Type of Participants | Number of Participants | Age of Participants (years) | Body Mass Index (BMI) (kg/m$^2$) | Fasting Plasma Glucose (FPG) (mmol/l) | IAP Conc. in stool (U/gm Stool) | Loss of IAP compared to Controls (%) |
|---|---|---|---|---|---|---|---|
| | Diabetic Patients | Total: 38 | 62.4 +/− 0.7 | 25.7 +/− 0.8 | 8.3 +/− 0.6 | 26.2 +/− 4.5 | 55.4 |
| | | Males: 15 | 63.7 +/− 1.0 | 26.4 +/− 1.5 | 7.2 +/− 0.9 | 20.7 +/− 6.9 | 59.0 |
| | | Females: 23 | 61.7 +/− 0.9 | 25.2 +/− 0.9 | 8.9 +/− 0.8 | 29.8 +/− 6.0 | 50.8 |
| | p Value (Controls vs Diabetics) | Total | 5.6E−01 | 1.5E−01 | 2.6E−12*** | 1.2E−03** | NA |
| | | Males | 9.6E−01 | 1.5E−01 | 1.5E−02* | 1.8E−02* | NA |
| | | Females | 2.4E−01 | 5.3E−01 | 4.0E−12*** | 2.6E−02* | NA |

Statistics: Values are expressed as mean+/−SEM. Statistical significance of the difference between two groups was tested using the unpaired two-tailed Student's t-Test, p<0.05 is considered significant. p<0.05; , p<0.01; *, p<0.001, NA, not applicable.

FIG. 3 is a graph showing that IAP levels are less in the stools of diabetic patients compared to the healthy controls.

Figure 3A:
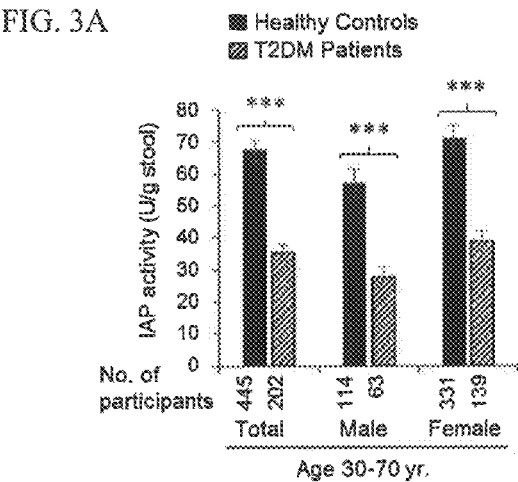
FIGS. 3A-C are graphs showing that patients with type 2 diabetes mellitus (T2DM) have low levels of intestinal alkaline phosphatase (IAP) in their stool.
Figure 3B:
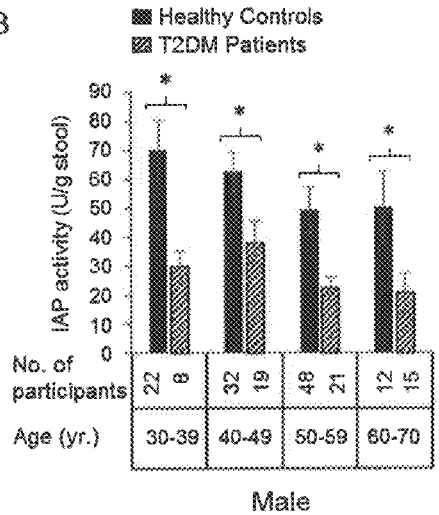
Figure 3C:
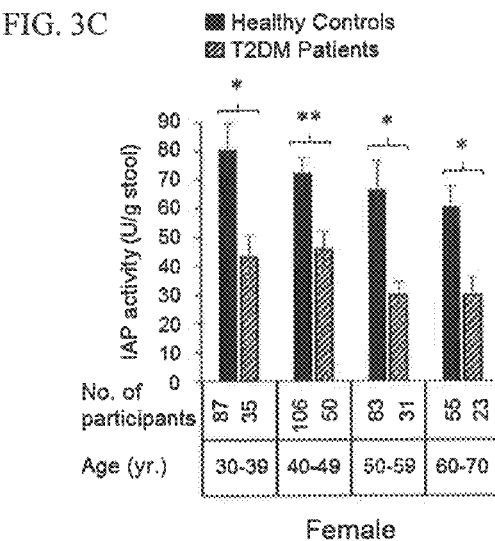

Comparison of IAP levels between the control healthy population and diabetic patients showed that on average the entire (total) diabetic population has much less IAP in their stools (FIG. 3A). Gender-matched distribution showed that both male and female diabetic patients have less stool IAP compared to their healthy counterparts (FIG. 3). Age group- and gender-matched distributions of IAP also showed that the enzyme apparently decreases with age both in males (FIG. 3B) and females (FIG. 3C) of non-diabetic and diabetic populations.

FIG. 3: Patients with type 2 diabetes mellitus (T2DM) have low levels of intestinal alkaline phosphatase (IAP) in their stool. Stool samples of healthy participants and T2DM patients were assayed for IAP concentration using an automatic biochemistry analyzer (see FIG. 2). (A) IAP concentrations in the stools of total non-diabetic healthy control and diabetic populations. (B) Age-dependent distribution of IAP concentrations in male control and diabetic populations. (C) Age-dependent distribution of IAP concentrations in female control and diabetic populations. Statistics: Values are expressed as mean+/−SEM. Statistical significance of the difference between two groups was tested using the unpaired two-tailed. Student's t-Test, p<0.05 is considered significant. *, p<0.05; , p<0.01; *, p<0.001. The post-hoc statistical power analyses revealed the powers for respective total, male and female groups to be 100%, 100% and 100%, respectively, validating the adequacy of power (conventionally, >80% power at α=0.05) for respective sample sizes. The difference in IAP values between younger and older groups of the same population (diabetic or non-diabetic) is not statistically significant.

Figure 4:
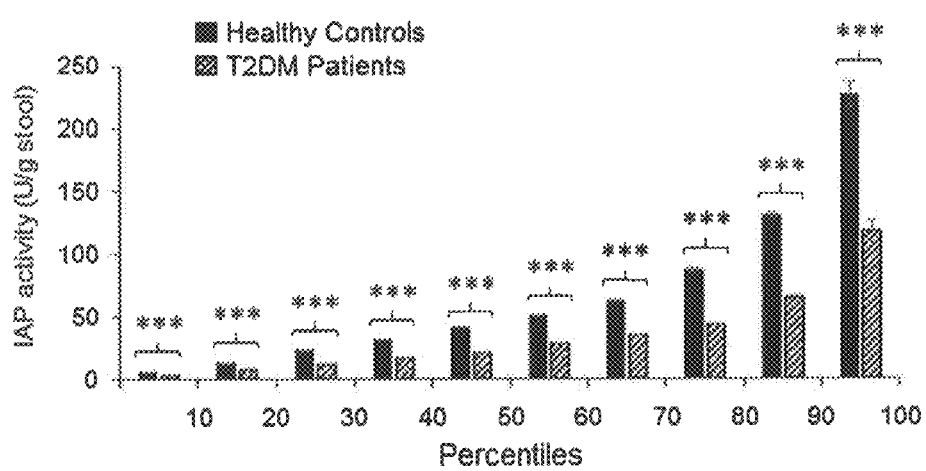
FIG. 4 is a graph showing that stool IAP levels are low in T2DM patients at all percentile points.

FIG. 4 is a graph showing that IAP levels are low in T2DM patients at all percentile points.

Taking in consideration of any influence of 'outliers' (few extremely high or low individual values compared to most values) in the average (mean) values of IAP levels as shown above (FIG. 3A), we further verified the difference in IAP levels of diabetic and non-diabetic groups at different percentile points. We evaluated the percentile distribution of IAP values in 202 T2DM patients and 445 healthy controls. We organized individual IAP values of each group (diabetic or non-diabetic) from the lowest to the highest, and then calculated the average IAP value within each 10 percentile divisions. It is apparent that at all percentile points IAP values are less in T2DM patients compared to the healthy population, and the difference is highly significant. The percentile distribution of IAP levels confirms that T2DM patients, indeed, have lower levels of IAP compared to their counterparts.

FIG. 4: IAP levels are low in T2DM patients at all percentile points. Individual IAP values from each group (Healthy Controls or T2DM Patients) were arranged from the lowest to the highest, and then the average IAP value within each 10$^{th}$ percentile was calculated (n=20 within each 10$^{th}$ percentile for T2DM Patients, and n=44 within each 10$^{th}$ percentile far Healthy Controls). Average values for corresponding percentiles are plotted. Statistics: Values are expressed as mean+/−SEM. Statistical significance of the difference between two respective groups was tested using the unpaired two-tailed Student's t-Test. p<0.05 is considered significant, *** p<0.001.

Example 4

IAP Deficiency is Associated with T2DM

Table 3 shows the Pearson correlation coefficient analysis between the IAP level and age, gender, FPG, BMI, ALT serum creatinine, blood pressure and lipid parameters. It is evident that there is no correlation between IAP and the above-mentioned T2DM risk factors.

TABLE 3

Pearson correlation coefficients showing no correlation of IAP levels with different risk factors of T2DM.

| | Type of participants | | | |
|---|---|---|---|---|
| | Male | | Female | |
| | Healthy | T2DM | Healthy | T2DM |
| Risk factors | IAP correlation | IAP correlation | IAP correlation | IAP correlation |
| Age | −0.192 | −0.221 | −0.08 | −0.131 |
| BMI | −0.024 | 0.088 | 0.085 | 0.008 |
| Creatinine | −0.013 | −0.069 | 0.07 | 0.055 |
| Total cholesterol | 0.267 | −0.132 | 0.004 | 0.127 |
| HDL-cholesterol | 0.101 | −0.007 | 0.005 | 0.206 |
| LDL-cholesterol | 0.176 | −0.130 | −0.014 | 0.080 |
| Triglycerides | 0.138 | 0.014 | −0.007 | 0.074 |
| ALT | 0.156 | 0.107 | −0.065 | −0.013 |
| FPG | −0.076 | 0.039 | 0.05 | −0.014 |
| Systolic blood pressure | 0.169 | −0.257 | −0.031 | −0.153 |
| Diastolic blood pressure | −0.040 | −0.059 | 0.039 | −0.060 |

Note: A Pearson correlation coefficient close to +1 or −1 indicates that the two variables are highly correlated (positively or negatively, respectively). A correlation coefficient between 0 and +0.30 or between 0 and −0.30 was considered of having no correlation between the two variables.

Table 4 shows a generalized linear regression model predicting a strong association of IAP with T2DM. It also predicts a mild association of IAP with age validating the observation that IAP decreases with age (see FIGS. 3B & C).

TABLE 4

A generalized linear regression model predicts an association of IAP with T2DM.

| Source | DF | Type III SS | F Value | Pr > F |
|---|---|---|---|---|
| Diabetes | 1 | 81665.66 | 23.3 | <0.0001 |
| Sex | 1 | 12309.33 | 3.51 | 0.0614 |
| FPG (mmol/l) | 1 | 180.46 | 0.05 | 0.8206 |
| BMI (kg/m$^2$) | 1 | 5335.29 | 1.52 | 0.2177 |
| Age | 1 | 23707.51 | 6.76 | 0.0095 |

Note: The model predicts a strong association of IAP with T2DM. It also predicts a mild association of IAP with age (IAP level gradually decreases with age; see FIGS. 3B & C).

Table 5 shows multiple logistic regression analyses predicting an independent inverse relationship between the IAP level and diabetes status. We performed multiple logistic regression analyses controlling for age, FPG, BMI, ALT, serum creatinine, blood pressure and lipid parameters. The data showed an independent inverse relationship between the IAP level and diabetes status (Table 5). With each 25 U/g, decrease in stool IAP, there is 35% increased risk of diabetes. We conclude that IAP deficiency is associated with diabetes independent of other known diabetic risk factors.

TABLE 5

Multiple logistic regression analyses predict an association of IAP deficiency with T2DM.

| Explanatory variables | Logistic coefficients per unit change | Odds ratio (95% CI) |
|---|---|---|
| Age (yr.) | 0.0226 | 1.023 (0.993-1.054) |
| Body mass index (BMI, kg/m$^2$) | 0.0466 | 1.048 (0.986-1.114) |
| Creatinine (mg/dl) | −0.0166 | 0.983 (0.847-1.142) |
| Total cholesterol (mg/dl) | 0.00183 | 1.002 (0.984-1.020) |
| HDL-cholesterol (mg/dl) | −0.0599 | 0.942 (0.900-0.985) |
| LDL-cholesterol (mg/dl) | 0.0206 | 1.021 (1.001-1.041) |
| Triglycerides (mg/dl) | 0.00473 | 1.005 (0.998-1.011) |
| ALT (U/l) | 0.00944 | 1.009 (0.998-1.021) |
| Systolic blood pressure (mmHg) | −0.00012 | 1.000 (0.984-1.016) |
| Diastolic blood pressure (mmHg) | −0.0139 | 0.986 (0.958-1.015) |
| FPG (mmol/l) | 1.3563 | 3.882 (2.972-5.070) |
| IAP (U/g stool) | −0.0145 | 0.986 (0.978-0.993) |

Note: With each U/g decrease in stool IAP level there is 1.4% increase in the odds of diabetes diagnosis. For example, if there is 25 U/g decrease in IAP level then there will be a 35% increased risk of diabetes. Statistics: Proc Logist procedure (SAS) was used for multiple logistic regression analyses determining association between T2DM with independent risk factors including IAP.

Example 5

Hyper- and Normo-Glycemic T2DM Patients have Similar Levels of Stool IAP

T2DM patients on rigorous antidiahetic medications and life-style changes very often achieve normoglycemic status (FPG<7.0 mmol/l). We were interested to know whether the glycemic status of diabetic patients has any effect on the stool IAP level.

Table 6 shows that both hyperglycemic (FPG>7.0 mmol/l) and normoglycemic diabetics have similar levels of IAP in their stools, and the difference in values between two respective groups is statistically insignificant.

TABLE 6

Hyper- and normo-glycemic diabetes patients have similar levels of stool IAP.

| | Type of Participants | Number of Participants | Age of Participants (years) | Body Mass Index (BMI) (kg/m$^2$) | Fasting Plasma Glucose (FPG) (mmol/l) | IAP Conc. (U/gm Stool) |
|---|---|---|---|---|---|---|
| Hyperglycemic diabetes patients (FPG > 7.0 mmol/l) | | Total: 119 | 47.0 +/− 0.9 | 25.9 +/− 0.4 | 10.3 +/− 0.3 | 37.7 +/− 3.4 |
| | | Males: 36 | 49.1 +/− 1.4 | 25.8 +/− 0.7 | 10.6 +/− 0.4 | 29.6 +/− 4.4 |
| | | Females: 83 | 46.1 +/− 1.1 | 26.0 +/− 0.5 | 10.1 +/− 0.3 | 41.3 +/− 4.4 |
| Normoglycemic diabetes patients (FPG < 7.0 mmol/l) | | Total: 83 | 48.3 +/− 1.1 | 26.1 +/− 0.5 | 5.2 +/− 0.1 | 32.0 +/− 3.8 |
| | | Males: 27 | 53.3 +/− 2.1 | 25.2 +/− 0.7 | 5.3 +/− 0.2 | 25.1 +/− 4.6 |
| | | Females: 56 | 45.9 +/− 1.2 | 26.5 +/− 0.7 | 5.2 +/− 0.1 | 35.2 +/− 5.2 |
| p Value (Hyperglycemic vs Normoglycemic) | Total | | 3.6E−01 | 7.9E−01 | 1.8E−33*** | 2.6E−01 |
| | Males | | 9.3E−02 | 6.0E−01 | 2.0E−14*** | 5.0E−01 |
| | Females | | 8.9E−01 | 5.3E−01 | 5.0E−21*** | 3.8E−03 |

Note: Diabetic patients were categorized into hyperglycemic (FPG>7.0 mmol/l) and normoglycemic (FPG<7.0 mmol/l) groups, and respective stool IAP levels were compared. Statistics: Values are expressed as mean+/−SEM. Statistical significance of the difference between two groups was tested using the unpaired two-tailed Student's t-Test. p<0.05 is considered significant. ***, p<0.001.

Example 6

High Levels of IAP is Protective Against Diabetes Irrespective of Body Mass Index (BMI)

It is well recognized that overweight (BMI>25.0 kg/m$^2$) and obese (BMI>30.0 kg/m$^2$) populations are more vulnerable for developing T2DM than the population with normal weights (BMI<25.0–18.5 kg/m$^2$). We categorized the diabetics as well as healthy controls of this study in two groups, one with BMI>25.0 kg/m$^2$ and the other having BMI<25.0 kg/m$^2$.

Table 7 shows that a high level of IAP is protective against diabetes irrespective of body mass index (BMI). It is evident that both groups of diabetics (BMI>25.0 kg/m$^2$ and BMI<25.0 kg/m$^2$) have significantly lower amounts of IAP compared to their healthy counterparts. These data suggest that IAP plays a protective role against the development of T2DM. An obese or overweight person with high IAP does not develop T2DM. Both groups of diabetes patients have similar levels of IAP, and the difference is statistically insignificant (p=0.77). We also observed that the levels of IAP in both groups of healthy controls are similar and the difference is insignificant (p=0.29).

and low-BMI groups of diabetic patients. Obese people with high stool IAP have no T2DM.

Example 7

The Majority of Population has the Incipient Metabolic Syndrome

IAP deficiency causes the metabolic syndrome in mice (Kaliannan et al. Proc Natl Acad Sci USA 2013; 110(17): 7003-8). Thus we predict that the association of IAP deficiency with T2DM in humans would be useful to isolate the people with 'the incipient metabolic syndrome' who are apparently healthy persons, however, vulnerable to develop the metabolic syndrome in the near future due to IAP deficiency. Victims of 'the incipient metabolic syndrome' should include the persons with 'incipient' diabetes, heart

TABLE 7

A high level of IAP is protective against diabetes irrespective of body mass index (BMI).

| Group | Type of Participants | Number of Participants | Age of Participants (years) | Body Mass Index (BMI) (kg/m$^2$) | Fasting Plasma Glucose (FPG) (mmol/l) | IAP Conc. in stool (U/gm stool) | Loss of IAP compared to Controls (%) |
|---|---|---|---|---|---|---|---|
| High BMI (>25.0 kg/m$^2$) | Healthy Controls | Total: 227 | 45.7 +/− 0.6 | 28.8 +/− 0.2 | 4.5 +/− 0.1 | 66.5 +/− 4.4 | NA |
| | | Males: 49 | 47.8 +/− 1.2 | 27.4 +/− 0.3 | 4.5 +/− 0.1 | 52.0 +/− 7.3 | NA |
| | | Females: 178 | 45.1 +/− 0.7 | 29.2 +/− 0.3 | 4.4 +/− 0.1 | 70.5 +/− 5.2 | NA |
| | Diabetic Patients | Total: 101 | 48.0 +/− 1.0 | 29.3 +/− 0.4 | 8.1 +/− 0.3 | 36.5 +/− 3.5 | 45.1 |
| | | Males: 28 | 52.5 +/− 1.9 | 28.7 +/− 0.7 | 8.3 +/− 0.6 | 29.0 +/− 5.1 | 44.2 |
| | | Females: 73 | 46.3 +/− 1.0 | 29.5 +/− 0.5 | 8.0 +/− 0.4 | 39.4 +/− 4.4 | 44.1 |
| | p Value (Controls vs Diabetics) | Total | 3.5E−02* | 2.7E−01 | 5.6E−41*** | 2.3E−05*** | NA |
| | | Males | 3.3E−02* | 3.9E−02* | 2.6E−11*** | 3.0E−02* | NA |
| | | Females | 3.5E−01 | 5.4E−01 | 1.2E−30*** | 3.6E−04*** | NA |
| Low BMI (<25.0 kg/m$^2$) | Healthy Controls | Total: 217 | 48.5 +/− 0.7 | 22.4 +/− 0.1 | 4.4 +/− 0.1 | 63.0 +/− 4.0 | NA |
| | | Males: 66 | 49.0 +/− 1.1 | 22.5 +/− 0.2 | 4.4 +/− 0.1 | 61.3 +/− 5.7 | NA |
| | | Females: 151 | 48.2 +/− 0.8 | 22.4 +/− 0.2 | 4.4 +/− 0.1 | 63.8 +/− 5.2 | NA |
| | Diabetic Patients | Total: 101 | 47.1 +/− 1.0 | 22.7 +/− 0.2 | 8.3 +/− 0.4 | 34.2 +/− 3.7 | 45.8 |
| | | Males: 35 | 49.6 +/− 1.6 | 23.1 +/− 0.3 | 8.3 +/− 0.6 | 26.6 +/− 4.1 | 56.6 |
| | | Females: 66 | 45.8 +/− 1.3 | 22.5 +/− 0.2 | 8.0 +/− 0.4 | 38.2 +/− 5.2 | 40.1 |
| | p Value (Controls vs Diabetics) | Total | 2.5E−01 | 1.9E−01 | 4.1E−39*** | 9.9E−06*** | NA |
| | | Males | 7.6E−01 | 1.8E−01 | 5.0E−14*** | 6.9E−05*** | NA |
| | | Females | 1.1E−01 | 5.4E−01 | 2.4E−26*** | 3.4E−03** | NA |

Note: There was no significant difference in IAP levels between high- and low-BMI groups of healthy controls as well as no significant difference between high- and low-BMI groups of diabetic patients. Obese people with high stool IAP do not develop T2DM. Statistics: Values are expressed as mean+/−SEM. Statistical significance of the difference between two groups was tested using the unpaired two-tailed Student's t-Test, p<0.05 is considered significant. *, p<0.05; , p<0.01; *, p<0.001. NA, not applicable.

Figure 5:
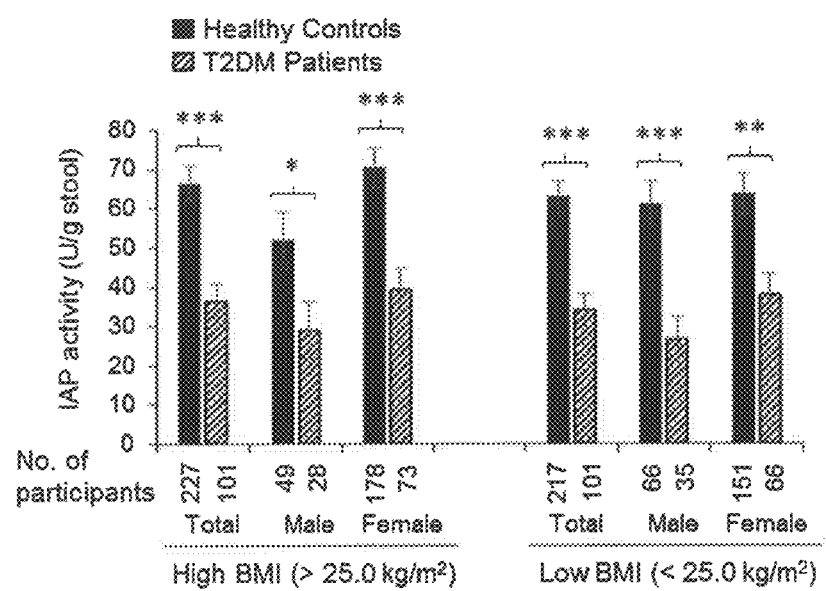
FIG. 5 is a graph showing that high levels of stool IAP is protective against T2DM irrespective of body mass index (BMI).

FIG. 5 is a graph showing the distributions of IAP in diabetes patients and healthy control subjects with high and low body mass index (BMI) as described in Table 7.

FIG. 5: High levels of IAP is protective against T2DM irrespective of body mass index (BMI). Stool samples of healthy participants and T2DM patients were assayed for IAP concentrations using an automatic biochemistry analyzer (see FIG. 3). The healthy controls as well as T2DM patients were categorized in two groups, one with high BMI (>25.0 kg/m2) and the other having low BMI (<25.0 kg/m2). Statistics: Values are expressed as mean+/−SEM. Statistical significance of the difference between two groups was tested using the unpaired two-tailed Student's t-Test, p<0.05 is considered significant. *, p<0.05; , p<0.01; *, p<0.001. Note: There was no significant difference in IAP levels between high- and low-BMI groups of healthy controls as well as no significant difference in IAP levels between high-disease, nonalcoholic fatty liver, hypertension, and other metabolic disorders. We observed that the average IAP level in healthy population is approx. 67.4+/−3.2 U/g stool (Table 1), and hence we define that a healthy person having IAP level less than 65.0 U/g stool, using the current assay condition, should be considered as having 'the incipient metabolic syndrome' that should include 'incipient diabetes' and 'the pre-metabolic syndrome (exhibiting at least one criterion of the metabolic syndrome)'. It is noteworthy that the numerical value of concentration of 65.0 U phosphatase per gm stool would vary depending on different alkaline phosphatase (AP) assays as well as on assay conditions, for example change of pH, time, temperature, substrate concentration, etc.

Table 8 shows that approx. 65% of the healthy population have 'the incipient metabolic syndrome' having IAP level<65.0 U/g stool. This prevalence rate is in concordance with the 71% prevalence rate of the pre-metabolic syndrome (exhibiting at least one criterion of the metabolic syndrome) (Al-Qahtani D A, Imtiaz M L. Prevalence of metabolic syndrome in Saudi adult soldiers. Saudi Med J 2005; 26(9): 1360-6). Also, it was reported that 68-81% of Pakistani people have low levels of HDL-cholesterol, one criterion of the metabolic syndrome (Basit A, Shera A S. 2008. Prevalence of metabolic syndrome in Pakistan. Metab Syndr Relat Disord. 6(3):171-5). We calculated that approx. 40% of healthy subjects have amounts of IAP that are less than the average IAP value of the diabetic group (35.0 U/g stool). It is predicted that these people have 'the severe incipient metabolic syndrome' and are extremely vulnerable to develop T2DM or other metabolic disorders within a few years. Interestingly, the prevalence rate of 'overt' metabolic syndrome (co-existence of 3 criteria of the metabolic syndrome; Huang P L. A comprehensive definition for metabolic syndrome. Dis Model Mech 2009; 2(5-6):231-7) is also 40% (Kaliannan et al. Proc Natl Acad Sci USA 2013; 110(17):7003-8; Ford. Diabetes Care. 2005 November; 28(11):2745-9).

Also, a few T2DM patients (approx. 15%) have stool IAP level>67.0 U/g (the average value of healthy controls), and this observation means that either IAP is not associated with the pathogenesis of T2DM in these specific patients or a persistent loss of IAP from a previously high level might also lead to T2DM. A loss of approx. 50% IAP activity might be significant to precipitate T2DM as diabetic patients on average have approx. 50% less IAP compared to their healthy counterparts (see Table 1 and FIG. 3). Thus it appears that a distinct population of incipient diabetics might also have higher IAP levels.

An incipient diabetic person is an apparently healthy person having a stool IAP level less than 65.0 U/gm stool using the assay conditions disclosed herein or previously having a higher IAP level but presently experiencing persistent loss of 50% IAP activity.

TABLE 8

The majority of population has the incipient metabolic syndrome.

| Group | Characteristics of Participants | |
|---|---|---|
| Healthy Controls | Average IAP level (U/g stool) | 67.4 +/− 3.2 |
| | Total number of Healthy Controls | 445 |
| | Number of Controls with IAP levels < 65.0 U/g stool (Incipient Metabolic Syndrome) | 299 |
| | Number of Controls with IAP levels > 65.0 U/g stool | 146 |
| | Percentage (%) of Incipient Metabolic Syndrome (299/445*100) | 67.2 |

Note: Based on the average IAP value of 67.4±/−3.2 U/g stool in healthy controls, it is defined that a healthy person with 'the incipient metabolic syndrome' has stool IAP levels<65.0 U/g stool. The incipient metabolic syndrome should also include 'incipient diabetes'.

What is claimed is:

1. A method for aiding in the diagnosis of incipient diabetes comprising measuring concentration of phosphatase in a stool sample from a subject, said stool sample including stool sample supernatant and stool sample suspension, wherein said stool sample is collected at multiple recurring time points, and wherein said measuring comprises:
   providing a substrate for phosphatase in a solid or liquid form;
   contacting, directly or indirectly, said substrate for phosphatase with the stool sample;
   waiting a specified period of time to allow an enzymatic reaction to occur between the substrate for phosphatase and the stool sample;
   quantifying a concentration of phosphatase in said stool sample; and
   comparing the concentration of phosphatase in said stool sample at an earlier one of the time points to the concentration at a later one of the time points wherein a decrease in phosphatase concentration indicates a presence of incipient diabetes in the subject
   or comparing the concentration of phosphatase in said stool sample to a normal range wherein a concentration below the normal range indicates a presence of incipient diabetes in the subject.

2. The method of claim 1, wherein said multiple recurring time points comprise daily, weekly, monthly or yearly.

3. The method of claim 1, wherein said subject is a human, cattle, pig, sheep, goat, cow, horse, dog, cat, monkey, rabbit, rat, mouse, chicken, or turkey.

4. The method of claim 3, wherein said subject is a human.

5. The method of claim 1, wherein said
   quantifying the concentration of phosphatase in said stool sample comprises quantifying the concentration of phosphatase in said stool sample using a spectrophotometer, a biochemistry analyzer, a high-performance liquid chromatography (HPLC) machine, a colorimeter, a luminometer or a mechanical, biochemical, electrical or electronic device.

6. The method of claim 1, wherein said substrate for phosphatase is attached to a solid medium.

7. The method of claim 6, wherein said solid medium comprises a membrane, a stick, a bead, a tube, a bottle, a slide, a swab, paper, glass, plastic, or wood.

8. The method of claim 7, wherein said membrane is nylon or nitrocellulose.

9. The method of claim 1, wherein said stool sample is attached to a solid medium.

10. The method of claim 9, wherein said solid medium comprises a membrane, a stick, a bead, a tube, a bottle, a slide, a swab, paper, glass, plastic, or wood.

11. The method of claim 10, wherein said membrane is nylon or nitrocellulose.

12. The method of claim 1, wherein said substrate for phosphatase comprises p-nitrophenyl phosphate, 5-Bromo-4-chloro-3-indolyl phosphate/nitro blue tetrazolium substrate system, Fast Red TR/Naphthol substrate system, CDP-star substrate (2-chloro-5-(4-methoxyspiro {1,2-dioxetane-3,2'(5'-chloro)-tricyclo [3.3.1.13.7]decan}-4-yl)-1-phenyl phosphate disodium salt) or combinations thereof.

13. The method of claim 1, wherein said phosphatase comprises an alkaline phosphatase, intestinal alkaline phosphatase, placental alkaline phosphatase, nonspecific tissue alkaline phosphatase (liver/bone/kidney alkaline phosphatase), germ cell alkaline phosphatase, neutrophil alkaline phosphatase, an acid phosphatase, stool alkaline phosphatase, bacterial alkaline phosphatase, or a peptide with phosphatase activity.

14. The method of claim 13, wherein said phosphatase is intestinal alkaline phosphatase or stool alkaline phosphatase.

15. The method of claim 13, wherein said phosphatase is a native intestinal alkaline phosphatase, a recombinant intestinal alkaline phosphatase, a mutant intestinal alkaline phosphatase, a peptide with intestinal alkaline phosphatase activity, a recombinant peptide with intestinal alkaline phosphatase activity, a native human intestinal alkaline phosphatase, recombinant human intestinal alkaline phosphatase, native calf intestinal alkaline phosphatase or recombinant calf intestinal alkaline phosphatase.

* * * * *